United States Patent [19]

Frihart

[11] Patent Number: 4,568,495
[45] Date of Patent: Feb. 4, 1986

[54] FRACTIONATION OF POLYMERIZED FATTY ACIDS

[75] Inventor: Charles R. Frihart, Lawrenceville, N.J.

[73] Assignee: Union Camp Corporation, Wayne, N.J.

[21] Appl. No.: 495,096

[22] Filed: May 16, 1983

[51] Int. Cl.$^4$ .............................. C09F 5/10; C11B 3/00
[52] U.S. Cl. ................................ 260/428.5; 260/412; 260/412.8; 260/428
[58] Field of Search ...................... 260/412, 412.8, 428, 260/428.5

[56] References Cited

U.S. PATENT DOCUMENTS

| | | | |
|---|---|---|---|
| 3,064,018 | 11/1962 | Bruera | 260/412.8 X |
| 3,923,847 | 12/1975 | Roselius et al. | 260/412.8 |
| 3,969,196 | 7/1976 | Losel | 203/49 |
| 4,280,961 | 7/1981 | Schneider et al. | 260/412.8 |
| 4,367,178 | 1/1983 | Heigel et al. | 260/412.8 X |

FOREIGN PATENT DOCUMENTS 2032789 5/1983 United Kingdom .

Primary Examiner—Helen M. S. Sneed
Attorney, Agent, or Firm—Kane, Dalsimer, Kane, Sullivan and Kurucz

[57] ABSTRACT

Polymeric fatty acids are fractionated by extraction with supercritical fluid solvents.

4 Claims, 2 Drawing Figures

FRACTIONATION OF POLYMERIZED FATTY ACIDS

BACKGROUND OF THE INVENTION

1. Field of the Invention

The invention relates to methods for the fractionation of polymeric mixtures and more particularly relates to methods of separating the various polymer components of polymerized fatty acids.

2. Brief Description of the Prior Art

Polymeric fatty acids are prepared by the polymerization of fatty acids, using techniques well known to those skilled in the art; see for example the polymerization described in U.S. Pat. No. 3,157,681. These polymeric fatty acids are sometimes referred to in the art as "dimer fatty acids" because the predominant constituent is the dimer of the fatty acid. However, the polymerized fatty acids are complex mixtures, containing unreacted monomeric compounds, trimer forms and higher polymeric forms of the fatty acids.

Commercially available polymeric fatty acids prepared from tall oil fatty acids are representative of polymeric fatty acids and may have a composition as follows:

|  | % BY WEIGHT |
| --- | --- |
| $C_{18}$ monobasic acids (monomer) | 0–5 |
| $C_{36}$ dibasic acids (dimer) | 60–95 |
| $C_{54}$ and higher polybasic acids (trimer) | 1–35 |

The relative ratios of monomer, dimer and trimer in unfractionated polymeric fatty acids are dependent on the nature of the starting material and the conditions of polymerization.

Heretofore, fractionation of the polymeric fatty acids to separate the monomer and dimer-trimer components has been done by conventional distillation and molecular distillation, and the separation of dimer and trimer components only by molecular distillation. These techniques are of course costly procedures and are adversely impacted upon by any ash in the dimerization product.

The method of the present invention provides a relatively inexpensive means to fractionate polymeric fatty acids.

The employment of solvent gases as liquids in their near critical state and as fluids in the supercritical state as extracting solvents has been previously described; see for example Francis, Physical Chem, 58, 1099 (1954) and Ind. Eng. Chem. 47, 230 (1955). Near critical and supercritical fluids, including hydrocarbon gases have been suggested as solvents for a wide range of materials; see for example U.S. Pat. No. 3,969,196. Despite the fact that the solvation properties of gases in their near critical and supercritical states and especially of hydrocarbon gases, has been known, the application of this knowledge has not been applied to the fractionation of polymeric fatty acids.

SUMMARY OF THE INVENTION

The invention comprises a method of separating fatty acid monomer, dimer and trimer from polymerized fatty acid mixtures, which comprises; extracting first the monomer, then the dimer and finally the trimer from the mixture in a supercritical fluid solvent or solvents, or by extracting all the components and selectively releasing the trimer, the dimer and finally the monomer from the supercritical gas stream.

BRIEF DESCRIPTION OF THE DRAWING

The accompanying drawing of FIG. 1 is a schematic representation of apparatus employed in the method of the invention to fractionate the polymeric fatty product with supercritical fluid solvents.

DETAILED DESCRIPTION OF THE PREFERRED EMBODIMENTS OF THE INVENTION

The method of the invention is carried out by bringing the polymeric fatty acid mixture in contact with a supercritical fluid solvent so as to fractionate the monomer, dimer and trimer components based upon their solubility in the supercritical fluid solvent or solvents. A wide variety of gases which are solvents in the supercritical fluid state may be employed. Representative of such gases are the hydrocarbon gases such as methane, ethane, propane, butane, ethylene, propylene and the like. Preferably, hydrocarbon gases are employed as the supercritical solvent fluids to fractionate dimer and trimer. Carbon dioxide may also be used in the supercritical fluid state and is preferred to fractionate the monomer compounds. The conditions under which such gases become supercritical fluids are well known to those skilled in the art as is apparatus for their manufacture and use in the extraction of organic materials; see for example the teachings set forth in the U.S. Pat. Nos. 3,969,196 and 4,308,200. The supercritical fluids are brought into contact with the polymeric fatty acids in a suitable vessel, under supercritical fluid conditions. Preferably, hydrocarbon gases are employed as the supercritical solvent fluids.

Figure 1:
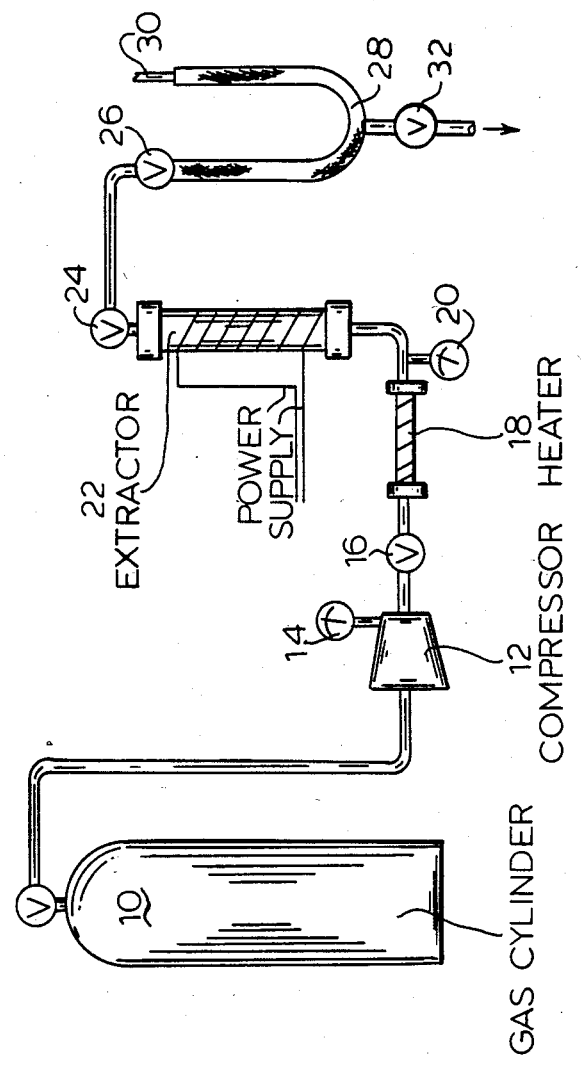
Figure 2:
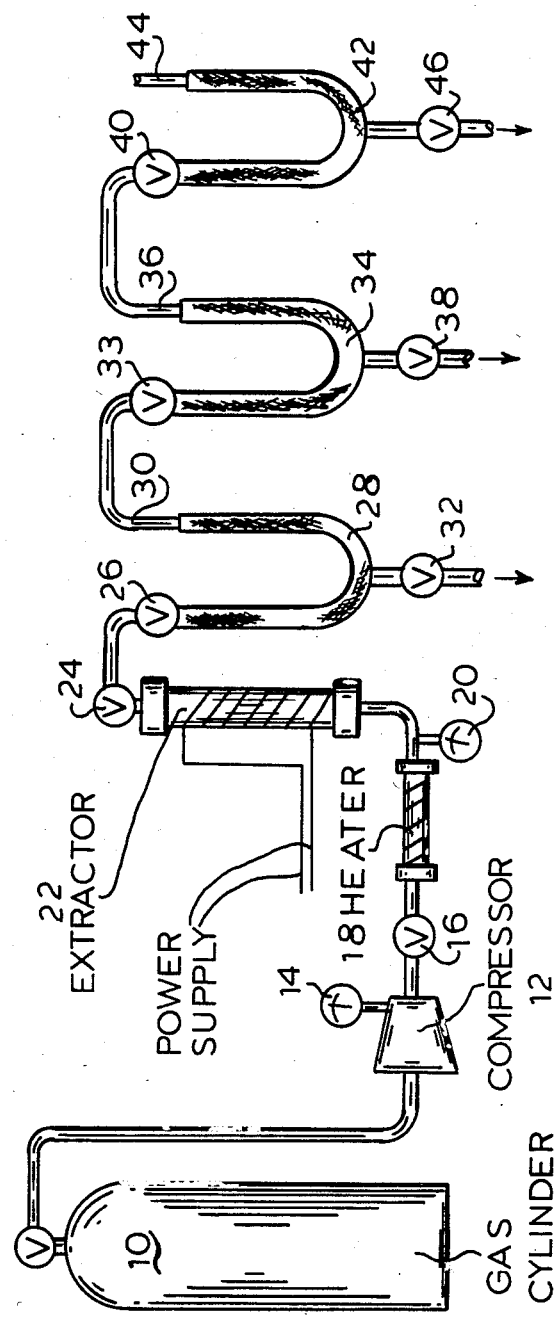
FIG. 2 is a schematic representation of apparatus employed in an alternative method of the invention.

The FIG. 1 of the accompanying drawings is a schematic representation of an apparatus, simple in nature, which may be employed in the method of the invention and because of its simplicity serves to exemplify the method of the invention. As shown in the accompanying drawing, a source of a suitable gas in the cylinder 10 may be fed by conduits into a compressor 12 wherein it is compressed to supercritical pressure conditions. The gas selected is one which in the supercritical state will preferentially dissolve one of the monomer, dimer or trimer components of the polymerized fatty acid over the remaining components. Preferably the pressure is within the range of from about 3000 to 5000 psi. A pressure gauge 14 monitors the compression and valve 16 provides a means for delivery of the compressed fluid to a heater 18 where the temperature of the compressed fluid is raised to a supercritical temperature. Preferably the temperature is within the range of from about 0° to about 200° C. Temperature gauge 20 monitors the heating of the compressed fluid which is then passed into an extractor vessel 22 which is provided with an electrical resistance heater means for maintaining the supercritical temperature. Previous to introduction of the supercritical gas into extractor vessel 22, the vessel 22 is charged with a quantity of polymeric fatty acid for extraction. When the supercritical fluid selected is one which will dissolve monomer compounds from the polymerized fatty acid mixture and it is introduced into the charged extractor vessel 22, extraction of monomer from the polymer mixture begins immediately. The monomer extract with the supercritical fluid is carried through expansion valves 24 and 26 to reduce the supercritical pressure of the gas. Upon dropping the pressure of the mixture below the supercritical pressure for the fluid, the extracted monomer is dropped from solution in the supercritical fluid, remaining in the separator tube 28 as the reduced pressure gaseous solvent is vented through end 30 of separator tube 28. Of course, the vented gas can be reused in a continuous process by recycling the gas back to the compressor 12 through outlet 30. The extracted liquid monomer product is then removed from the apparatus by opening valve 32. This process may be continued for a sufficient time to remove most of the monomer. Then the pressure or temperature of the supercritical extraction fluid may be increased or the fluid itself is changed so as to preferentially extract the dimer following the general procedure described above. The final changes in conditions of higher pressure or temperature or of a different supercritical fluid solvent then allows for the isolation of trimer, again following the same general procedure described above.

An alternative procedure employing the apparatus shown would be to carry out the extraction using conditions or a supercritical fluid solvent that will extract all the components (monomer, dimer and trimer). Then by partially reducing the pressure and/or temperature through valves 24 and 26, the trimer drops from solution first and is collected from valve 33. Then the supercritical fluid containing dimer and monomer goes through a second stage reduction in temperature and/or pressure at valve 33 to drop from solution the dimer in separator tube 34 than can be collected from valve 38. A final reduction in the temperature and/or pressure of the supercritical fluid would cause the monomer to drop from the fluid in separator tube 42 and the monomer is collected from the valve 46. The supercritical fluid could be recycled back from the outlet 44 to the compressor 12.

The following example describes the manner and process of making and using the invention and sets forth the best mode contemplated by the inventor for carrying out the invention but is not to be construed as limiting.

An experiment to fractionate crude polymerized fatty acid using several supercritical fluids was conducted employing the apparatus described above and shown in the accompanying drawing of FIG. 1. The extractor vessel 22 was loaded with 5.93 grams of polymerized fatty acid shown by gas-phase chromatography to comprise 2.7 percent monomer, 80.7 percent dimer and 16.6 percent trimer (% peak height). The charged extractor vessel was heated to a temperature of 60° C. and then compressed carbon dioxide at a pressure of 3200 psi, heated to temperature of 60° C., was allowed to enter the extractor vessel and contact the crude polymer mixture present. The compressed gas was passed through the extractor vessel and then allowed to expand at 1 atmosphere pressure immediately prior to entering the separating tube 28 described above. Visual observation of material being deposited in the separator was an indication of material solubility and extraction.

The above procedure was repeated a number of times, on the residue of the preceding charge but employing a variety of temperatures, pressures and supercritical fluids. The gases, temperatures, pressures and extracts obtained are reported in the TABLE BELOW.

TABLE

| Gas Used | Temp. (°C.) | Pressure (psi) | Amount Extracted (gm) | ANALYSIS % Peak Height (GPC) Relative | | |
|---|---|---|---|---|---|---|
| | | | | Monomer | Dimer | Trimer |
| $CO_2$ | 60 | 3200 | 0.09 | 29.2 | 70.8 | — |
| $CO_2$ | 60 | 3700–5500 | 0.35 | — | 96.6 | 3.4 |
| $CO_2$ | 70 | 6500 | 0.19 | 13.3 | 80.7 | 6 |
| $C_2H_4$ | 70 | 2000–5000 | 0.98 | — | 93.7 | 6.3 |
| $C_2H_4$ | 70 | 5500 | 2.4 | — | 90.2 | 9.8 |
| $C_2H_4$ | 77 | 5500 | 1.56 | — | 80.4 | 19.6 |
| $C_3H_8$ | 107 | 2000–5000 | 0.5 | — | 24.2 | 75.8 |
| $C_3H_8$ | 107 | 5000 | 0.1 | — | 22.8 | 77.2 |

What is claimed:

1. A method of separating fatty acid monomer, dimer and trimer from polymerized fatty acid mixtures containing said monomer, dimer and trimer, which comprises; extracting at least one of said monomer, dimer and trimer from the mixture, with a supercritical fluid solvent for the one to be extracted, leaving a residue which comprises at least one of said monomer, dimer and trimer which is insoluble in said solvent.

2. The method of claim 1 which comprises separating fatty acid monomer, dimer and trimer from polymerized fatty acid mixtures containing said monomer, dimer and trimer, by
   (a) extracting one of the monomer, dimer and trimer from the mixture, in a first supercritical fluid solvent, leaving a first residue;
   (b) extracting one of the monomer, dimer and trimer not extracted in step (a) from the first residue in a second supercritical fluid solvent, leaving a second residue; and
   (c) extracting one of the monomer, dimer and trimer not extracted in steps (a) or (b) from the second residue in a third supercritical fluid solvent.

3. The method of claim 2 wherein the first supercritical fluid solvent is supercritical carbon dioxide at a temperature of circa 60° C. and under a pressure of 3200 to 6500 psi; the second supercritical fluid solvent is supercritical ethylene at a temperature of circa 70° C. and under a pressure of 2000 to 5000 psi; and the third supercritical fluid is supercritical propylene at a temperature of circa 107° C. and under a pressure of 2000 to 5000 psi.

4. The method of claim 1 which comprises separating fatty acid monomer, dimer and trimer from polymerized fatty acid mixtures containing said monomer, dimer and trimer, by
   extracting the monomer, dimer and trimer from the mixtures in a supercritical fluid solvent; and
   reducing the pressure and/or the temperature of said extract whereby one of said monomer, dimer and trimer becomes insoluble therein and separates from the other of said monomer, dimer and trimer.

* * * * *